United States Patent
Rejai et al.

(10) Patent No.: US 6,511,452 B1
(45) Date of Patent: Jan. 28, 2003

(54) TAMPON APPLICATOR WITH IMPROVED FINGERGRIP

(75) Inventors: Jamshid Rejai, Dover, DE (US); Robert Norquest, Dover, DE (US); Michael L. Miller, Dover, DE (US)

(73) Assignee: Playtex Products, Inc., Westport, CT (US)

( * ) Notice: Subject to any disclaimer, the term of this patent is extended or adjusted under 35 U.S.C. 154(b) by 0 days.

(21) Appl. No.: 09/957,921

(22) Filed: Sep. 21, 2001

(51) Int. Cl.⁷ .................................................. A61F 13/20
(52) U.S. Cl. ......................................................... 604/15
(58) Field of Search ........................... 604/11–18, 57, 604/59, 60

(56) References Cited

U.S. PATENT DOCUMENTS

| | | | |
|---|---|---|---|
| 2,489,502 A | 11/1949 | Ruth ........................... 128/270 |
| 2,587,717 A | 3/1952 | Fourness .................... 128/263 |
| 2,922,423 A | 1/1960 | Rickard et al. ............. 128/263 |
| 3,204,635 A | * 9/1965 | Voss et al. |
| 3,534,737 A | * 10/1970 | Jones, Sr. |
| 3,543,754 A | * 12/1970 | Jones, Sr. |
| 3,575,169 A | 4/1971 | Voss et al. ................... 128/263 |
| 3,628,533 A | 12/1971 | Loyer ........................... 128/263 |
| 3,895,634 A | 7/1975 | Berger et al. ................ 128/263 |
| 4,412,833 A | 11/1983 | Wiegner et al. ............... 604/14 |
| 4,573,963 A | 3/1986 | Sheldon ........................ 604/15 |
| 4,573,964 A | 3/1986 | Huffman ....................... 604/15 |
| 4,891,042 A | 1/1990 | Melvin et al. ................. 604/18 |
| 5,290,501 A | 3/1994 | Klesius ........................ 264/322 |
| 5,395,308 A | 3/1995 | Fox et al. ...................... 604/15 |
| 5,709,652 A | 1/1998 | Hagerty ........................ 604/15 |
| 5,931,803 A | 8/1999 | Jackson ........................ 604/15 |
| 6,019,743 A | 2/2000 | Cole et al. .................... 604/15 |
| 6,045,526 A | 4/2000 | Jackson ........................ 604/15 |
| 6,322,531 B1 | * 11/2001 | Cortese et al. |

* cited by examiner

Primary Examiner—Dennis Ruhl
(74) Attorney, Agent, or Firm—Ohlandt, Greeley, Ruggiero & Perle, LLP

(57) ABSTRACT

A tampon applicator is provided that comprises a tubular barrel adapted to house a pledget and a telescoping plunger adapted to expel the pledget out of the barrel. A portion of the applicator has a fingergrip area with at least one multi-directional gripping structure to enhance the gripping characteristics of the applicator. The multi-directional gripping structure allows the user to securely hold the applicator during insertion of the applicator into the vagina, expulsion of the pledget from the barrel of the applicator, and removal of the applicator from the vagina.

30 Claims, 4 Drawing Sheets

TAMPON APPLICATOR WITH IMPROVED FINGERGRIP

BACKGROUND OF THE INVENTION

1. Field of the Invention

The present invention relates to an insertion device capable of housing an insertable element. More particularly, the present invention relates to a catamenial insertion device, such as a tampon applicator, having a distinct fingergrip area with at least one multi-directional gripping structure.

2. Description of the Prior Art

A catamenial insertion device or applicator normally has two components, namely a barrel and a plunger that is adapted to telescopically slide in the barrel. The material to be expelled from the applicator, such as an absorbent pledget, is positioned in the barrel of the applicator. The barrel has a first end for ejection of the pledget, and a second end for receipt of the plunger. To use the tampon applicator, the consumer will position the ejection end appropriately, grasp the barrel, and move or slide the plunger in the barrel towards the first end of the barrel to expel the pledget.

Absorbent tampon pledgets exert a pressure on the inside wall of the applicator barrel. Thus, expulsion of the pledget from the barrel requires an applicator with a gripping configuration conducive to secure holding by the user with minimal pressure being applied to the barrel. By minimizing the pressure applied to the barrel of the applicator, deformation of the barrel is reduced. Deformation causes significant friction amongst the pledget, the barrel, and the plunger, which significantly impedes the expulsion of the pledget from the barrel.

Various fingergrip configurations disposed on the barrel of an applicator have been proposed to facilitate handling and placement of the applicator, and expulsion of the pledget into the vagina. One approach is a tampon applicator having an integral fingergrip that is formed by embossing an outside surface of the barrel of the tampon applicator. The embossed portion of the applicator barrel typically takes the form of a series of raised circumferential rings or a series of discrete raised dots aligned in several circumferential rows. Examples of such fingergrips can be found in U.S. Pat. No. 6,045,526 to Jackson; U.S. Pat. No. 5,395,308 to Fox et al.; U.S. Pat. No. 5,290,501 to Klesius; U.S. Pat. No. 4,573,964 to Huffman; U.S. Pat. No. 4,573,963 to Sheldon; U.S. Pat. No. 4,891,042 to Nelvin et al.; U.S. Pat. No. 4,412,833 to Wiegner et al.; U.S. Pat. No. 3,895,634 to Berger; U.S. Pat. No. 3,628,533 to Leyer; U.S. Pat. No. 2,922,423 Rickard et al; U.S. Pat. No. 2,587,717 to Fourness; and U.S. Pat. No. 2,489,502 to Ruth.

Another approach to the gripping problem is found in U.S. Pat. No. 3,575,169 to Voss et al., which provides separate raised elements that are applied to an outer tube of a tampon applicator to provide a fingergrip. The elements can be formed of plastic, rubber, ceramic, or other materials, and can either be affixed to the outer tube by interference fit or by bonding.

U.S. Pat. No. 4,536,178 to Lichstein et al. discloses a tampon applicator having flattened surfaces with a gripping structure on the flattened surface. However, the gripping structure disclosed is limited to rows of ribs.

While addressing the need for a gripping structure on an applicator for insertion of a pledget into the vagina, the prior art gives little weight to the need for that same gripping structure to be configured to also provide equal gripping ability upon removal of the applicator barrel from the vagina. Thus, there is a need for a tampon applicator with a distinct fingergrip area having at least one multi-directional gripping structure that allows a consumer to not only grip the applicator for insertion of the applicator and expulsion of the pledget with ease, but also grip the applicator for easy removal from the vagina.

SUMMARY OF THE INVENTION

It is an object of the present invention to provide a tampon applicator having a distinct fingergrip area with at least one multi-directional gripping structure.

It is another object of the present invention to provide such a tampon applicator where the at least one multi-directional gripping structure enables the user to securely grip the barrel of the applicator for insertion of the applicator and expulsion of the tampon pledget from the barrel with ease.

It is still another object of the present invention to provide such a tampon applicator where the at least one multi-directional gripping structure enables the user to grip the applicator and remove the applicator from the vagina with ease.

It is yet another object of the present invention to provide such a tampon applicator where the at least one multi-directional gripping structure is one or more slits, perforations, lances, or any combinations thereof.

It is a further object of the present invention to provide such a tampon applicator where the at least one multi-directional gripping structure may be raised, depressed, or a combination thereof.

It is still a further object of the present invention to provide such a tampon applicator having a distinct fingergrip area with at least one multi-directional gripping structure that is easy to manufacture.

These and other objects and advantages of the present invention will be appreciated from a tampon according to the present invention. The tampon includes an absorbent pledget and an applicator for housing the pledget. The applicator comprises a barrel adapted to house the pledget and a telescoping plunger adapted to expel the pledget from the barrel. A portion of the applicator, preferably the barrel, has a fingergrip area. The fingergrip area has at least one multi-directional gripping structure to enhance the gripping characteristics of the applicator. The multi-directional gripping structure allows the user to securely hold the applicator during insertion of the applicator into the vagina, expulsion of the pledget from the barrel of the applicator, and removal of the applicator from the vagina.

DETAILED DESCRIPTION OF THE INVENTION

Figure 1:
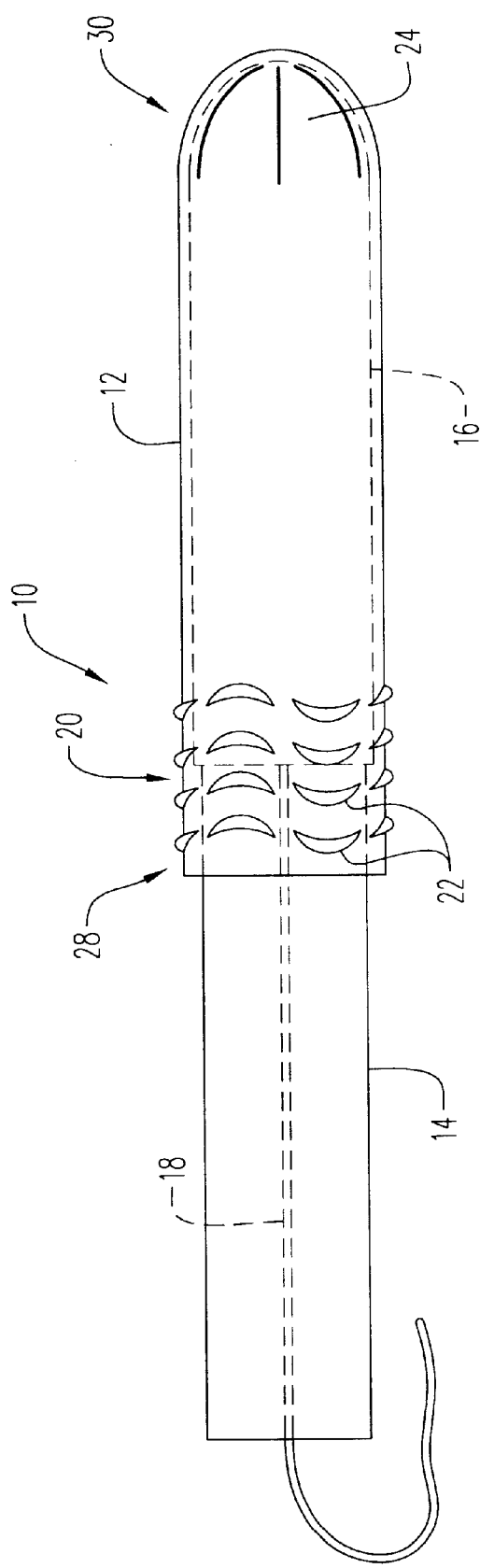
FIG. 1 is a perspective view of a preferred embodiment of the tampon applicator of the present invention.

Referring to the drawings, and in particular FIG. 1, a tampon applicator of the present invention is generally represented by reference numeral 10. Applicator 10 has a barrel 12 and a plunger 14 that is adapted to telescopically move or slide in the barrel. The configuration and diameter of the inside of barrel 12 and the exterior surface of plunger 14 is such that the plunger telescopically, and preferably without friction, slides in barrel 12, yet plunger 14 has enough of a diameter to eject pledget 16 from the barrel. Thus, barrel 12 and plunger 14 preferably have the same configuration, especially at plunger receiving end 28 of the barrel. While this configuration can be any configuration, nonetheless, barrel 12 and plunger 14, preferably, have a cylindrical or circular configuration.

Absorbent pledget 16 is housed in barrel 12, and has a withdrawal string 18. Barrel 12 has a front or ejection end 30 and a rear or plunger receiving end 28. The ejection end 30 may be open-ended or may have three to eight separate or connected petals, which provide increased comfort to the user during insertion and removal of applicator 10. When the insertion end 30 of the applicator 10 has petals 24, the petals enclose the pledget 16 during insertion of applicator 10 into the vagina, resulting in increased comfort to the user.

To enhance gripping of barrel 12, a fingergrip area 20 is disposed on or in the outside surface of barrel 12. In a preferred embodiment, fingergrip area 20 is disposed about the circumference or outer surface of barrel 12. More preferably, fingergrip area 20 is disposed adjacent plunger receiving end 28.

Fingergrip area 20 has at least one, and more preferably two or more gripping structures. The gripping structures are any multi-directional gripping structures. For example, the gripping structures are preferably one or more lances, slits, perforations, or any combinations thereof. The gripping structures may be raised above the outer surface of barrel 12, depressed below the outer surface of barrel 12, constructed so as the tip of the gripping structure aligns with the outer surface of barrel 12, or any combinations thereof. The gripping structures may be patterned or arranged in any configuration and in any number suitable for creating an enhanced gripping area for a user's fingers.

Preferably, the two or more gripping structures are arranged substantially in columns or rows extending axially from the plunger receiving end 28 to ejection end 30 of barrel 12. To provide multi-directional gripping, the two or more gripping structures are disposed in a first, insertion direction in one or more columns and in a second, removal direction, substantially opposite the first direction, in one or more remaining columns. As a result, a tampon user naturally places their finger(s) on the column(s) having the gripping structures disposed in the same direction as the applicator, i.e., insertion direction during insertion of the applicator and removal direction during removal of the applicator.

When a user's fingers cover or contact multiple columns where the gripping structures are disposed in both the insertion and removal directions, the user not only experiences enhanced grippability in the direction of travel of the applicator as a result of those gripping structures disposed in that same direction, the gripping structures disposed in the opposite direction also provide additional friction, which also enhances grippability of the applicator. As a result, the multi-directional gripping structures ensure that a user can insert an applicator, eject a pledget from the applicator, and remove an applicator with comfort and ease.

In a preferred embodiment of the present invention, as depicted in FIG. 1, the gripping structures are two or more lances 22 formed in an arcuate configuration. With this configuration, each column of arcuate lances in the axial direction, from the ejection end 30 of barrel 12 to the plunger receiving end 28 of the barrel, is disposed in a first, insertion direction and a second, substantially opposite second direction in adjacent columns, thereby providing a multi-directional gripping structure. Each arcuate lance 22 is preferably sheared into the outer surface of barrel 12, creating a cut through the entire thickness of the barrel. The raised edge of each arcuate lance creates an edge or shoulder, which results in an effective gripping structure. By alternating the direction of the arcuate lances in each column, the edge or shoulder is formed in an opposite direction in each column, thus providing effective gripping in both the insertion direction and removal direction of applicator 10.

While FIG. 1 depicts each column with arcuate lances 22 disposed in alternating axial directions, i.e., insertion and removal directions, the columns may be arranged such that two or more adjacent columns have gripping structures disposed in the same direction with two or more subsequent adjacent columns having gripping structures disposed in a substantially opposite direction. It should be understood that the columns of gripping structures can be arranged in any pattern such that a suitable number of gripping structures are disposed in opposite directions to one another to ensure adequate axial gripping ability in both the insertion and removal directions.

It should be understood that the gripping structures may be arranged in any number of columns practical, given the circumference of the applicator barrel and/or fingergrip area. Preferably, the fingergrip area has two or more multi-directional gripping structures arranged in about 4 to about 8 columns. When a smaller number of columns is used, i.e., about 4, the columns may be arranged such that diametrically opposed columns have gripping structures arranged in the same direction. Such an arrangement naturally urges a user's fingers to grip the columns having the gripping structures disposed in the intended direction of the applicator. This results in greater ease of use of the applicator to the consumer.

It should also be understood that each gripping structure in any given substantial column may vary slightly in size, dimension and/or shape from other gripping structures in that same column.

Each arcuate lance preferably has a width between about 0.10 inches to about 0.35 inches. More preferably, each arcuate lance has a width between about 0.15 inches to about 0.25 inches. In addition, each arcuate lance forms a raised edge or shoulder having a height about 0.01 inches to about 0.06 inches, and more preferably between about 0.02 inches to about 0.03 inches.

Figure 2:
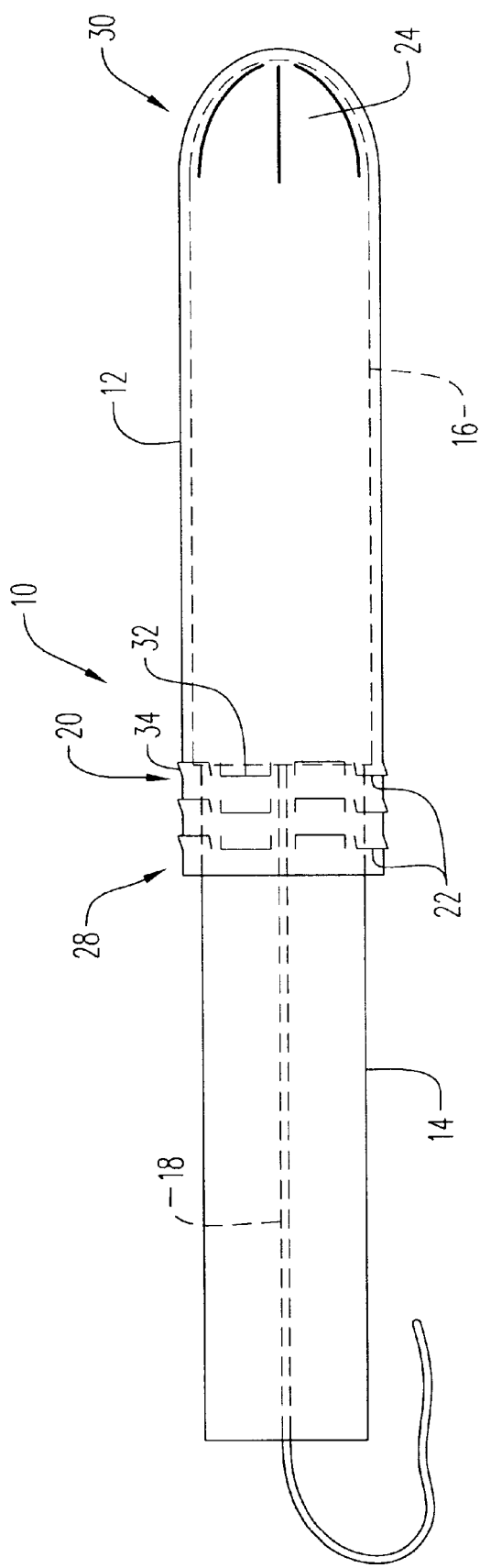
FIG. 2 is a perspective view of another embodiment of the tampon applicator of the present invention.

Referring to FIG. 2, which is a second embodiment of the present invention, the plurality of gripping structures are straight lances or slits 22. Each straight lance is formed such that the shoulder 32 of each lance 22 is substantially straight across. Each lance 22 is preferably sheared with a notch 34 at each end of shoulder 32, which allows each lance 22 to become raised or depressed relative to the outer surface of barrel 12 upon formation. By alternating the direction of the straight lances in each column, the edge or shoulder is formed in an opposite direction in each column, thus providing effective gripping in both the insertion direction and removal direction of applicator 10. It should be understood that the straight lances can be arranged or patterned in any configuration and in any number suitable for creating an enhanced gripping area, as set forth above for the arcuate lance embodiment.

Also, it should be understood that a tampon applicator can be formed with a fingergrip area having any combination of straight lances and arcuate lances. These lances can be arranged or patterned in any configuration and in any number suitable for creating an enhanced gripping area.

The applicator barrel 12 of the present invention can be made from a material, such as, for example, paper, paper laminate, paper-based, plastic, or any combinations thereof. Preferably, the applicator barrel is made from paper-based material. The paper-based material used in making the applicator can be a single layer of material, or two or more laminated layers. Suitable paper-based materials for the formation of the applicator barrel include, for example, paperboard, cardboard, cup stock, paper slurry, biopolymer, spiral wound tube, or any combinations thereof. The paper material used to form the barrel may also be coated with one or more coating materials. Suitable coating materials include, for example, plastic, wax, silicone, biopolymer, cellophane, nitrocellulose, lacquer, epoxy, or any combinations thereof.

Figure 3A:
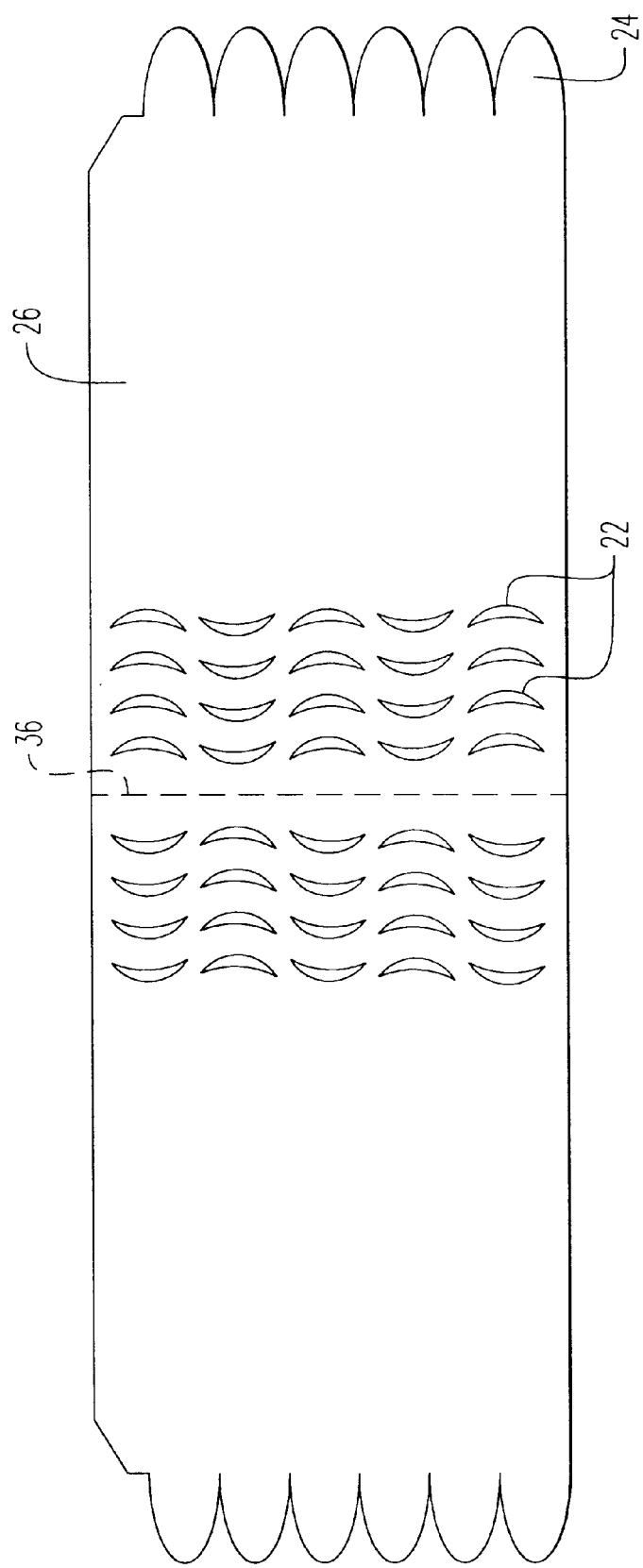
FIG. 3A is a plan view of an applicator barrel blank prior to forming the preferred embodiment of the applicator barrel of the present invention.
Figure 3B:
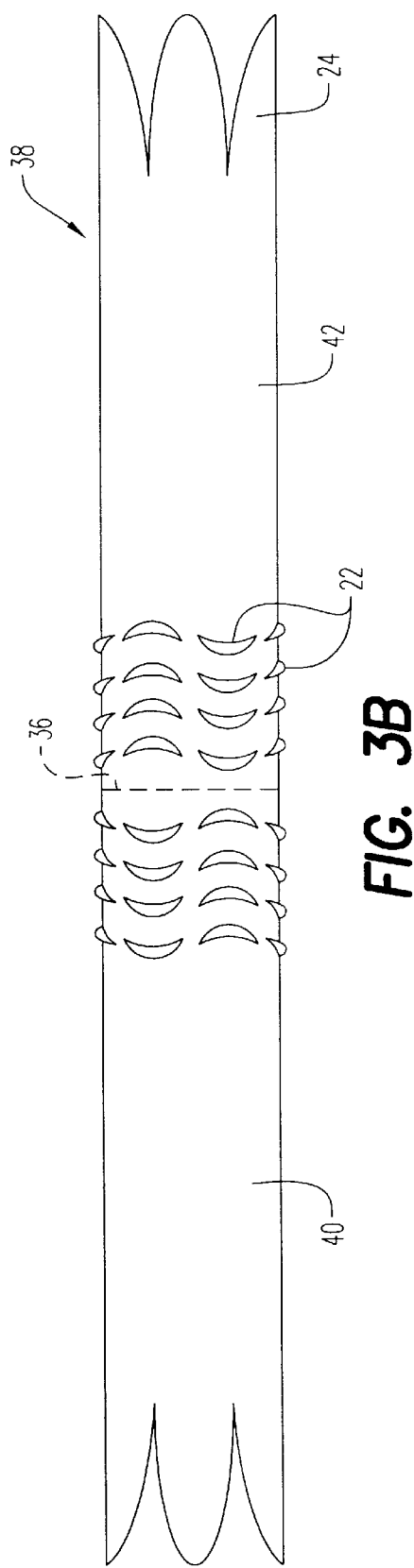
FIG. 3B is a plan view of the applicator barrel blank in FIG. 3A formed into a barrel, but prior to forming the preferred embodiment of the applicator barrel of the present invention.

The gripping structures of the present invention may be formed on applicator barrel 12 by any known method in the art. However, referring to the drawings, and in particular FIGS. 3A and 3B, the preferred arcuate gripping structures of the present invention are preferably formed on a flat cardboard applicator barrel tube blank 26. The arcuate gripping structures 22 are lanced or sheared in barrel tube blank 26 prior to forming the blank into a tubular barrel. Once the gripping structures are formed on barrel tube blank 26, it is formed into a tube 38 and then it is cut vertically along line 36 to form two separate tubes 40, 42. When applicator barrel tube blank 26 is formed into barrel tubes 40, 42, each arcuate lance forms a raised edge or shoulder, like scales on a fish, which provides gripping ability to the user. In another embodiment of the present invention (not shown), the lancing or shearing of the arcuate gripping structures is done on a spiral wound tube applicator barrel.

Tampon pledgets 14, and notably radially expanding tampon pledgets, are capable of exerting increased forces on applicator barrel 12, making it difficult for a tampon user to expel the pledget into the vagina. Once the consumer has expelled pledget 14 into the vagina from barrel 12, it is equally important that the consumer have a suitable gripping ability on applicator 10 to easily overcome removal forces exerted on the applicator by the vaginal walls and remove the applicator from the vagina.

In summary, a woman can securely and comfortably grasp, control and position the tampon applicator 10 of the present invention, during insertion of applicator 10, expulsion of absorbent pledget 16 housed therein, and subsequent removal of the applicator from the vagina, as a result of fingergrip area 20 formed with a multi-directional lanced gripping structure. The lanced gripping structure provides gripping ability axially in both the insertion and removal directions without the user having to change their grip on applicator barrel 12, so the user is able to easily maneuver, control and position the applicator.

The foregoing specification and drawings are merely illustrative of the present invention and are not intended to limit the present invention to the disclosed embodiments. Variations and changes, which are obvious to one skilled in the art, are intended to be within the scope and nature of the present invention as defined in the appended claims.

What is claimed is:

1. A tampon applicator comprising:
a barrel adapted to house a pledget and receive a plunger, said barrel having an outer surface and a fingergrip area disposed about a portion of said outer surface, said fingergrip area having at least two multi-directional gripping structures disposed on or in said fingergrip area, wherein at least one of said at least two multi-directional gripping structures is directed in a first direction and at least one other of said at least two multi-directional gripping structures is directed in a second direction substantially opposite said first direction.

2. The tampon applicator of claim 1, wherein said at least two multi-directional gripping structures provide gripping ability in said first and second directions, wherein said first direction is in an applicator insertion direction and said second direction is in an applicator removal direction substantially opposite said first direction.

3. The tampon applicator of claim 1, wherein said at least two multi-directional gripping structures are at least two lances.

4. The tampon applicator of claim 3, wherein said at least two multi-directional gripping structures are at least two straight lances, arcuate lances, or any combination thereof.

5. The tampon applicator of claim 3, wherein said at least two multi-directional gripping structures are at least two arcuate lances.

6. The tampon applicator of claim 5, wherein said at least two arcuate lances have a width between about 0.10 inches to about 0.35 inches.

7. The tampon applicator of claim 5, wherein said at least two arcuate lances have a height from about 0.01 inches to about 0.06 inches.

8. The tampon applicator of claim 5, wherein said at least two arcuate lances are a plurality of arcuate lances disposed in columns on said outer surface of said barrel.

9. The tampon applicator of claim 8, wherein said plurality of arcuate lances are disposed in each column in a direction substantially opposite that of said arcuate lances disposed in an adjacent column.

10. The tampon applicator of claim 8, wherein said plurality of arcuate lances are disposed in two or more columns in a direction substantially opposite that of said arcuate lances disposed in two or more subsequent additional adjacent columns.

11. The tampon applicator of claim 1, wherein said at least two multi-directional gripping structures are raised above, depressed below, flush with, or any combinations thereof, with respect to said outer surface of said barrel.

12. The tampon applicator of claim 1, wherein said barrel is formed from a material selected from the group consisting of paper, paper laminate, paper-based, plastic, paper slurry, biopolymer, and any combinations thereof.

13. The tampon applicator of claim 1, wherein said barrel is coated with a material selected from the group consisting of plastic, wax, silicone, biopolymer, cellophane, nitrocellulose, lacquer, epoxy, and any combinations thereof.

14. The tampon applicator of claim 1, wherein said barrel further comprises three to eight petals formed on an ejection end of said barrel.

15. A method for making a tampon applicator barrel having at least two multi-directional gripping structures disposed thereon, the method comprising the steps of:
(a) providing a tampon applicator barrel blank;
(b) forming said at least two multi-directional gripping structures on at least a portion of said applicator barrel blank; and
(c) forming said applicator barrel blank into an applicator barrel, wherein at least one of said at least two multi-directional gripping structure is directed in a first direction and at least one other of said at least two multi-directional gripping structures is directed in a second direction substantially opposite said first direction.

16. The method of claim 15, wherein said at least two multi-directional gripping structures provide gripping ability in said first and second directions, wherein said first direction is in an applicator insertion direction and said second direction is in an applicator removal direction substantially opposite said first direction.

17. The method of claim 15, wherein said at least two multi-directional gripping structures are two or more lances.

18. The method of claim 15, wherein said at least two multi-directional gripping structures are straight lances, arcuate lances, and any combination thereof.

19. The method of claim 15, wherein said at least two multi-directional gripping structures are raised above, depressed below, flush with, and any combinations thereof, with respect to an outer surface of said barrel.

20. The method of claim 15, wherein said at least two multi-directional gripping structures are a plurality of multi-directional gripping structures disposed in columns on said portion of said applicator barrel blank.

21. The method of claim 20, wherein said plurality of multi-directional gripping structures are disposed in one or more columns in a direction substantially opposite that of said plurality of multi-directional gripping structures disposed in one or more subsequent additional adjacent columns.

22. The method of claim 15, wherein said applicator barrel blank is formed from a material selected from the group consisting of paper, paper laminate, paper-based, plastic, paper slurry, biopolymer, and any combinations thereof.

23. The method of claim 15, wherein said applicator barrel blank is coated with a coating material selected from the group consisting of plastic, wax, silicone, biopolymer, cellophane, nitrocellulose, lacquer, epoxy, and any combinations thereof.

24. The method of claim 15, wherein said barrel comprises three to eight petals formed on an ejection end of said barrel.

25. A method for making a tampon applicator barrel having at least two arcuate lance gripping structures disposed circumferentially thereon, the method comprising the steps of:

(a) providing a tampon applicator barrel blank;

(b) shearing at least two arcuate lance fingergrip structures on a portion of said applicator barrel blank; and (c) forming said applicator barrel blank into an applicator barrel, wherein at least one of said at least two arcuate lance gripping structures is directed in a first direction and at least one other of said at least two arcuate lance gripping structures is directed in a second direction substantially opposite said first direction, and wherein said at least two arcuate lance fingergrip structures are raised, thus providing a gripping ability in both said insertion direction and said removal direction.

26. The method of claim 25, wherein said at least two arcuate lance gripping structures are a plurality of arcuate lance gripping structures disposed in one or more columns on said portion of said barrel.

27. The method of claim 26, wherein said plurality of arcuate lance gripping structures are disposed in two or more columns and said plurality of lance gripping structures are disposed in each column in a direction substantially opposite that of said arcuate lance gripping structures disposed in an adjacent column.

28. The method of claim 27, wherein said plurality of arcuate lance gripping structures are disposed in two or more columns in a direction substantially opposite that of said plurality of arcuate lance gripping structures disposed in two or more subsequent additional adjacent columns.

29. The method of claim 25, wherein said applicator barrel blank is formed from a material selected from the group consisting of paper, paper laminate, paper-based, plastic, paper slurry, biopolymer, and any combinations thereof.

30. The method of claim 25, wherein said applicator barrel blank is coated with a material selected from the group consisting of plastic, wax, silicone, biopolymer, cellophane, nitrocellulose, lacquer, epoxy, and any combinations thereof.

* * * * *